US008609396B2

(12) United States Patent
Kim et al.

(10) Patent No.: US 8,609,396 B2
(45) Date of Patent: Dec. 17, 2013

(54) MICROORGANISM PRODUCING O-ACETYL-HOMOSERINE AND THE METHOD OF PRODUCING O-ACETYL-HOMOSERINE USING THE MICROORGANISM

(75) Inventors: So Young Kim, Gwacheon-si (KR); Yong Uk Shin, Yongin-si (KR); In Kyung Heo, Seoul (KR); Hyun Ah Kim, Namwon-si (KR); Chang Il Seo, Incheon (KR); Ju Eun Kim, Seoul (KR); Sung Kwang Son, Seoul (KR); Sang Mok Lee, Seoul (KR); Sung Hoo Jhon, Seoul (KR); Han Jin Lee, Seoul (KR); Kwang Ho Na, Seoul (KR)

(73) Assignee: CJ Cheiljedang Corporation, Seoul (KR)

( * ) Notice: Subject to any disclaimer, the term of this patent is extended or adjusted under 35 U.S.C. 154(b) by 582 days.

(21) Appl. No.: 12/550,099

(22) Filed: Aug. 28, 2009

(65) Prior Publication Data

US 2011/0053252 A1 Mar. 3, 2011

(51) Int. Cl.
*C12N 1/21* (2006.01)
*C12P 13/06* (2006.01)

(52) U.S. Cl.
USPC ...................................... 435/252.33; 435/116

(58) Field of Classification Search
None
See application file for complete search history.

(56) References Cited

U.S. PATENT DOCUMENTS

| 2004/0199941 A1 | 10/2004 | San et al. ...................... 800/281 |
| 2009/0253186 A1 | 10/2009 | Kim et al. ..................... 435/116 |

FOREIGN PATENT DOCUMENTS

| WO | 2005/108561 A2 | 11/2005 |
| WO | 2007/077041 | 7/2007 |
| WO | 2007/116955 | 10/2007 |
| WO | 2008/013432 | 1/2008 |
| WO | 2008/039177 | 4/2008 |
| WO | 2008/127240 | 10/2008 |

OTHER PUBLICATIONS

Lee et al. (Protein Expr. Purif., 61:197-203, 2008; Author manuscript available online Jun. 27, 2008).*

Brown et al., "The Enzymic Interconversion of Acetate and Acetyl-coenzyme A in *Escherichia coli*," *Journal of General Microbiology*, 102 (1997): 327-336, 1977.

Browning et al., "Modulation of CRP-dependent transcription at the *Escherichia coli acs*P2 promoter by nucleoprotein complexes: anti-activation by the nucleoid proteins FIS and IHF," *Molecular Microbiology*, 51 (1): 241-254, 2004.

Hayashi et al., "Highly accurate genome sequences of *Escherichia coli* K-12 strains MG1655 and W3110," *Molecular Systems Biology*: 1-5, Epub Feb. 21, 2006.

Kumari et al., "Cloning, Characterization, and Functional Expression of *acs*, the Gene Which Encodes Acetyl Coenzyme A Synthetase in *Escherichia coli*," *Journal of Bacteriology*, 177 (10): 2878-2886, 1995.

Rock et al., "Role of Feedback Regulation of Pantothenate Kinase (CoaA) in Control of Coenzyme A Levels in *Escherichia coli*," *Journal of Bacteriology*, 185 (11): 3410-3415, 2003.

Song et al., "Kinetics and Regulation of Pantothenate Kinase from *Escherichia coli*," *The Journal of Biological Chemistry*, 269 (43): 27051-27058, 1994.

Krömer et al., "Metabolic pathway analysis for rational design of L-methionine production by *Escherichia coli* and *Corynebacterium glutamicum*," *Metabolic Engineering* 8:353-369, 2006.

Lin et al., "Acetyl-CoA synthetase overexpression in *Escherichia coli* demonstrates more efficient acetate assimilation and lower acetate accumulation: a potential tool in metabolic engineering," *Appl. Microbiol. Biotechnol.* 71:870-874, 2006.

Song et al., "Cloning, Sequencing, and Expression of the Pantothenate Kinase (*coa*A) Gene of *Escherichia coli*," *Journal of Bacteriology* 174(20):6411-6417, 1992.

Vallari et al., "Biosynthesis and Degradation Both Contribute to the Regulation of Coenzyme A Content in *Escherichia coli*," *Journal of Bacteriology* 170(9):3961-3966, 1988.

Dai et al., "Over-Expression, Purification and Characterization of Acetyl-CoA Synthetase from *Sinorhizobium meliloti*," Chinese Journal of Applied & Environmental Biology 10(1):113-115, 2004 (English abstract).

Zhang et al., "Expression, purification and enzyme activity determination of pantothenate kinase from *Mycobacterium tuberculosis*," Journal of the Fourth Military Medical University 27(23): 2135-2138, 2006 (English abstract).

English translation of Chinese Office Action, issued Aug. 27, 2012, for Chinese Application No. 201010144874.6, 10 pages.

* cited by examiner

*Primary Examiner* — Brian J Gangle

(74) *Attorney, Agent, or Firm* — Seed IP Law Group PLLC

(57) ABSTRACT

Disclosed herein are a microorganism strain capable of producing the L-methionine precursor O-acetyl homoserine in high yield and a method of producing O-acetyl homoserine using the same. The microorganism strain is a strain of *Escherichia* sp. in which an acetyl-CoA synthase gene (acs) and/or a pantothenate kinase gene (coaA) encoding a pantothenate kinase gene refractory to feedback inhibition by CoA is introduced and expressed.

10 Claims, 3 Drawing Sheets

SEQUENCE LISTING

```
<160> NUMBER OF SEQ ID NOS: 9

<210> SEQ ID NO 1
<211> LENGTH: 24
<212> TYPE: DNA
<213> ORGANISM: Artificial Sequence
<220> FEATURE:
<223> OTHER INFORMATION: Forward primer for acs

<400> SEQUENCE: 1
atcatgagcc aaattcacaa acac                                              24

<210> SEQ ID NO 2
<211> LENGTH: 32
<212> TYPE: DNA
<213> ORGANISM: Artificial Sequence
<220> FEATURE:
<223> OTHER INFORMATION: Reverse primer for acs

<400> SEQUENCE: 2
ctggcaaagc ttttacgatg gcatcgcgat ag                                     32

<210> SEQ ID NO 3
<211> LENGTH: 24
<212> TYPE: DNA
<213> ORGANISM: Artificial Sequence
<220> FEATURE:
<223> OTHER INFORMATION: Forward primer for coaA(R106A)

<400> SEQUENCE: 3
atcatgagta taaagagca aacg                                               24
```

<210> SEQ ID NO 4
<211> LENGTH: 33
<212> TYPE: DNA
<213> ORGANISM: Artificial Sequence
<220> FEATURE:
<223> OTHER INFORMATION: Reverse primer for coaA(R106A)

<400> SEQUENCE: 4
gcgcctgcaa tacggcggcg gttgtacttt tcc                          33

<210> SEQ ID NO 5
<211> LENGTH: 25
<212> TYPE: DNA
<213> ORGANISM: Artificial Sequence
<220> FEATURE:
<223> OTHER INFORMATION: Forward primer for coaA(R106A)

<400> SEQUENCE: 5
gccgtattgc aggcgctatt aagcc                                   25

<210> SEQ ID NO 6
<211> LENGTH: 33
<212> TYPE: DNA
<213> ORGANISM: Artificial Sequence
<220> FEATURE:
<223> OTHER INFORMATION: Reverse primer for coaA(R106A)

<400> SEQUENCE: 6
ctggcaaagc ttttatttgc gtagtctgac ctc                          33

<210> SEQ ID NO 7
<211> LENGTH: 1959
<212> TYPE: DNA
<213> ORGANISM: Escherichia coli W3110

<400> SEQUENCE: 7
atgagccaaa ttcacaaaca caccattcct gccaacatcg cagaccgttg cctgataaac      60
cctcagcagt acgaggcgat gtatcaacaa tctattaacg tacctgatac cttctggggc     120
gaacagggaa aaattcttga ctggatcaaa ccttaccaga aggtgaaaaa cacctccttt     180
gcccccggta atgtgtccat taaatggtac gaggacggca cgctgaatct ggcggcaaac     240
tgccttgacc gccatctgca agaaaacggc gatcgtaccg ccatcatctg ggaaggcgac     300
gacgccagcc agagcaaaca tatcagctat aaagagctgc accgacgt ctgccgcttc     360 gccaataccc tgctcgagct gggcattaaa aaaggtgatg tggtggcgat ttatatgccg     420
atggtgccgg aagccgcggt tgcgatgctg gcctgcgccc gcattggcgc ggtgcattcg     480
gtgattttcg gcggcttctc gccggaagcc gttgccgggc gcattattga ttccaactca     540
cgactggtga tcacttccga cgaaggtgtg cgtgccgggc gcagtattcc gctgaagaaa     600
aacgttgatg acgcgctgaa aaacccgaac gtcaccagcg tagagcatgt ggtggtactg     660
aagcgtactg gcgggaaaat tgactggcag gaagggcgcg acctgtggtg gcacgacctg     720
gttgagcaag cgagcgatca gcaccaggcg gaagagatga cgccgaaga tccgctgttt     780 attctctaca cctccggttc taccggtaag ccaaaaggtg tgctgcatac taccggcggt     840
tatctggtgt acgcggcgct gacctttaaa tatgtctttg attatcatcc gggtgatatc     900
tactggtgca ccgccgatgt gggctgggtg accggacaca gttacttgct gtacggcccg     960
ctggcctgcg gtgcgaccac gctgatgttt gaaggcgtac ccaactggcc gacgcctgcc    1020
cgtatggcgc aggtggtgga caagcatcag gtcaatattc tctataccgc acccacggcg    1080

```
atccgcgcgc tgatggcgga aggcgataaa gcgatcgaag gcaccgaccg ttcgtcgctg    1140
cgcattctcg gttccgtggg cgagccaatt aacccggaag cgtgggagtg gtactggaaa    1200
aaaatcggca acgagaaatg tccggtggtc gataccctggt ggcagaccga aaccggcggt    1260
ttcatgatca ccccgctgcc tggcgctacc gagctgaaag ccggttcggc aacacgtccg    1320
ttcttcggcg tgcaaccggc gctggtcgat aacgaaggta accgctggc gggggccacc    1380 gaaggtagcc tggtaatcac cgactcctgg ccgggtcagg cgcgtacgct gtttggcgat    1440
cacgaacgtt ttgaacagac ctacttctcc accttcaaaa atatgtattt cagcggcgac    1500
ggcgcgcgtc gcgatgaaga tggctattac tggataaccg ggcgtgtgga cgacgtgctg    1560
aacgtctccg gtcaccgtct ggggacggca gagattgagt cggcgctggt ggcgcatccg    1620
aagattgccg aagccgccgt agtaggtatt ccgcacaata ttaaaggtca ggcgatctac    1680
gcctacgtca cgcttaatca cggggaggaa ccgtcaccag aactgtacgc agaagtccgc    1740
aactgggtgc gtaaagagat tggcccgctg gcgacgccag acgtgctgca ctggaccgac    1800
tccctgccta aacccgctc cggcaaaatt atgcgccgta ttctgcgcaa aattgcggcg    1860
ggcgatacca gcaacctggg cgatacctcg acgcttgccg atcctggcgt agtcgagaag    1920
ctgcttgaag agaagcaggc tatcgcgatg ccatcgtaa                          1959

<210> SEQ ID NO 8
<211> LENGTH: 316
<212> TYPE: PRT
<213> ORGANISM: Escherichia coli W3110

<400> SEQUENCE: 8

Met Ser Ile Lys Glu Gln Thr Leu Met Thr Pro Tyr Leu Gln Phe Asp
  1               5                  10                  15

Arg Asn Gln Trp Ala Ala Leu Arg Asp Ser Val Pro Met Thr Leu Ser
             20                  25                  30

Glu Asp Glu Ile Ala Arg Leu Lys Gly Ile Asn Glu Asp Leu Ser Leu
         35                  40                  45

Glu Glu Val Ala Glu Ile Tyr Leu Pro Leu Ser Arg Leu Leu Asn Phe
     50                  55                  60

Tyr Ile Ser Ser Asn Leu Arg Arg Gln Ala Val Leu Glu Gln Phe Leu
 65                  70                  75                  80

Gly Thr Asn Gly Gln Arg Ile Pro Tyr Ile Ile Ser Ile Ala Gly Ser
                 85                  90                  95

Val Ala Val Gly Lys Ser Thr Thr Ala Ala Val Leu Gln Ala Leu Leu
            100                 105                 110

Ser Arg Trp Pro Glu His Arg Arg Val Glu Leu Ile Thr Thr Asp Gly
        115                 120                 125

Phe Leu His Pro Asn Gln Val Leu Lys Glu Arg Gly Leu Met Lys Lys
    130                 135                 140

Lys Gly Phe Pro Glu Ser Tyr Asp Met His Arg Leu Val Lys Phe Val
145                 150                 155                 160

Ser Asp Leu Lys Ser Gly Val Pro Asn Val Thr Ala Pro Val Tyr Ser
                165                 170                 175

His Leu Ile Tyr Asp Val Ile Pro Asp Gly Asp Lys Thr Val Val Gln
            180                 185                 190

Pro Asp Ile Leu Ile Leu Glu Gly Leu Asn Val Leu Gln Ser Gly Met
        195                 200                 205

Asp Tyr Pro His Asp Pro His Val Phe Val Ser Asp Phe Val Asp
    210                 215                 220
```

```
Phe Ser Ile Tyr Val Asp Ala Pro Glu Asp Leu Leu Gln Thr Trp Tyr
225                 230                 235                 240

Ile Asn Arg Phe Leu Lys Phe Arg Glu Gly Ala Phe Thr Asp Pro Asp
                245                 250                 255

Ser Tyr Phe His Asn Tyr Ala Lys Leu Thr Lys Glu Glu Ala Ile Lys
                260                 265                 270

Thr Ala Met Thr Leu Trp Lys Glu Ile Asn Trp Leu Asn Leu Lys Gln
            275                 280                 285

Asn Ile Leu Pro Thr Arg Glu Arg Ala Ser Leu Ile Leu Thr Lys Ser
        290                 295                 300

Ala Asn His Ala Val Glu Glu Val Arg Leu Arg Lys
305                 310                 315

<210> SEQ ID NO 9
<211> LENGTH: 134
<212> TYPE: DNA
<213> ORGANISM: Artificial Sequence
<220> FEATURE:
<223> OTHER INFORMATION: pPro promoter

<400> SEQUENCE: 9
tcgagcatag catttttatc cataagatta gcggatctaa cctttacaat tgtgagcgct        60
cacaattatg atagattcaa ttgtgagcgg ataacaattt cacacagaat tcattaaaga       120
ggagaaaggt acat                                                         134
```

MICROORGANISM PRODUCING O-ACETYL-HOMOSERINE AND THE METHOD OF PRODUCING O-ACETYL-HOMOSERINE USING THE MICROORGANISM

BACKGROUND OF THE INVENTION

1. Field of the Invention

The present invention relates to a microorganism strain capable of producing O-acetyl homoserine, an L-methionine precursor, in high yield. More particularly, the present invention relates to a microorganism strain in which an acetyl-CoA synthase gene and/or a pantothenate kinase gene refractory to feedback inhibition by CoA is introduced and enhanced to produce O-acetyl homoserine in high yield. Also, the present invention is concerned with a method of producing O-acetyl homoserine in high yield using the microorganism strain.

2. Description of the Related Art

Methionine, an essential amino acid for the body, finds a variety of applications in the food and medical industries, such as the use thereof as an additive in animal feed and foods and as a material for parenteral nutrient solutions and medicines. Methionine acts as a precursor for choline (lecithin) and creatine and is used as a material useful for the synthesis of cysteine and taurine. Together with cysteine, methionine is one of two sulfur-containing proteinogenic amino acids. S-Adenosyl methionine, derived from L-methionine, serves as a methyl donor in vivo and is involved in the synthesis of various neurotransmitters in the brain. Methionine and/or S-adenosyl-L-methionine (SAM) is/are also found to prevent lipid accumulation in the liver and arteries and to alleviate depression, inflammation, liver diseases and muscle pain (Jeon B R et al., *J Hepatol.*, 2001 March; 34(3): 395-401).

As summarized below, methionine and/or S-adenosyl-L-methionine has been thus far known to have the in vivo functions of:

1) suppressing lipid accumulation in arteries and in the liver, where lipid metabolism is mediated, and improving blood circulation in the brain, the heart and the kidneys (J Hepatol. Jeon B R et al., 2001 March; 34(3): 395-401).

2) promoting the digestion, detoxication and excretion of toxic substances and the excretion of heavy metals such as Pb.

3) acting as an antidepressant when methionine is administered in a daily dose of from 800 to 1,600 mg (Am J Clin Nutr. Mischoulon D. et al., 2002 November; 76(5): 1158S-61S)

4) improving liver functions against liver diseases (FASEB J. Mato J M., 2002 January; 16(1): 15-26), particularly, against alcohol-induced liver injury (Cochrane Database Syst Rev., Rambaldi A., 2001; (4): CD002235)

5) showing an anti-inflammation effect on osteoarthritis and promoting the healing of joints (ACP J Club. Sander O., 2003 January-February; 138(1): 21, J Fam Pract., Soeken K L et al., 2002 May; 51(5): 425-30).

6) acting as an essential nutrient to hair to prevent brittle hair and depilation (Audiol Neurootol., Lockwood D S et al., 2000 September-October; 5(5): 263-266).

For use in animal feed, foods and medicines, methionine can be synthesized chemically or biologically.

In the chemical synthesis, on the whole, methionine is produced through the hydrolysis of 5-(β-methylmercaptoethyl)-hydantoin. However, the synthesized methionine is disadvantageously present in a mixture of L- and D-forms which needs a difficult additional process to separate them from each other. In order to solve this problem, the present inventors developed a biological method for selectively synthesizing L-methionine, a chemical which a patent (WO 2008/103432) has already been applied for. The method, termed in brief "a two-step process", comprises the fermentative production of an L-methionine precursor and the enzymatic conversion of the L-methionine precursor to L-methionine. The methionine precursor preferably includes O-acetylhomoserine and O-succinyl homoserine. The two-step process is evaluated on terms of having overcome the problems from which the conventional methods suffer, such as sulfide toxicity, feedback regulation in methionine synthesis by methionine and SAMe, and degradation of intermediates by cystathionine gamma synthase, O-succinylhomoserine sulfhydrylase and O-acetylhomoserine sulfhydrylase. Also, compared to the conventional chemical synthesis method of producing DL-methionine, the two-step process has the advantage of being selective for L-methionine only, with the concomitant production of organic acids, such as succinic acid and acetic acid as useful by-products.

Found as an intermediate in the biosynthesis pathway of methionine, O-acetyl-homoserine is used as a precursor for the production of methionine (WO 2008/013432). O-acetyl-homoserine is synthesized from L-homoserine and acetyl-CoA with the aid of O-acetyl transferase as shown in the following formula:

L-Homoserine+Acetyl-CoA O→Acetyl-Homoserine.

In the U.S. patent application Ser. No. 12/062,835 of the present assignee are disclosed a microorganism strain in which thrA and metX genes are introduced to improve the biosynthesis of L-homoserine and O-acetyl-homoserine, respectively, and a method for producing O-acetyl homoserine at high yield using the same. In this context, the present inventors conceived that the enrichment of acetyl-CoA, one of the two substrates used in the biosynthesis of O-acetyl-homoserine, would increase the production yield of O-acetyl homoserine.

In *E. coli*, acetyl-CoA is, for the most part, synthesized from pyruvate. However, if excess glucose is present, acetyl-CoA may be produced from the acetic acid accumulated in the medium. The synthesis of acetyl-CoA from acetic acid may take advantage of two different biosynthesis pathways. In the one acetyl-CoA biosynthesis pathway, an acetyladenylate (AcAMP) intermediate is found through which acetyl-CoA synthase (ACS) activates acetate to acetyl-CoA. In the other pathway, acetic acid is converted through acetyl phosphate to acetyl-CoA as a result of the consecutive reactions catalyzed by acetate kinase (ACK) and phosphotransacetylase (PTA) (JOURNAL OF BACTERIOLOGY, May 1995, p. 2878-2886). Having a high affinity for acetate, acetyl-CoA synthase, which plays a pivotal role in the biosynthesis pathway mediated thereby, can activate acetate even at a low intracellular or extracellular level to acetyl-CoA. In contrast, the ACK-PTA-mediated acetyl-CoA biosynthesis pathway is operated only at a high acetate level, which may result from the fermentation of mixed acids, because the enzymes have a low affinity for acetate (J. Gen. Microbiol. 102:327-336.).

As for the acetyl-CoA synthase, its expression is inhibited at the transcription level by catabolite repression control until the exponential growth due to the CRP-binding site located upstream of the promoter and since then, its expression increases when the cell enters the stationary phase (Mol. Microbiol. 2004 January; 51(1):241-54.).

Thus, the acetate accumulated in the middle phase of fermentation can be activated to acetyl-CoA through the ACK-PTA pathway. However, if there is a low level of acetate, acetyl-CoA is converted to acetate because the ACK-PTA pathway is reversible. That is, the depletion of acetyl-CoA may occur during the ACK-PTA pathway, showing a negative effect on the synthesis of O-acetyl homoserine.

Accordingly, in order to utilize the acetate produced during fermentation, efforts are made to increase the activity of acetyl-CoA synthase. The increase of acetyl-CoA synthase activity allows the acetate accumulated in the media to be rapidly converted into acetyl-CoA, resulting in an improvement in the production of O-acetyl homoserine.

Coenzyme A (CoA), used as a substrate, together with acetate, in the biosynthesis of acetyl-CoA, is a representative acyl group carrier within cells. Coenzyme A is synthesized in a series of processes from pantothenate with enzymatic catalysis for each process as follows. First, pantothenate kinase (CoaA) activates pantothenate (Vitamin B5) to 4'-phosphopantothenate to which a cysteine is then added to form 4'-phosphopantothenoyl-L-cysteine, followed by decarboxylation to 4'-phosphopantetheine by the cooperation of P-PanCys synthase/P-PanCys decarboxylase (coaBC). Subsequently, 4'-phosphopantetheine is adenylylated to form dephospho-CoA by the enzyme phosphopantetheine (P-PanSH) adenylyltransferase (coaD). Finally, dephospho-CoA is phosphorylated using ATP to coenzyme A by the enzyme dephosphocoenzyme A (deP-CoA) kinase (coaE).

Generally, CoA is a cofactor for a multitude of metabolic reactions as well as many synthetic reactions within cells. For this reason, its pool is maintained at a constant level by regulation mechanisms. The primary key player in regulating the intracellular CoA pool is pantothenate kinase, which catalyzes the first committed step and is the rate-controlling enzyme in CoA biosynthesis. The regulation of pantothenate kinase activity by feedback inhibition is the critical factor controlling the intracellular CoA concentration (J Biol. Chem. 1994 Oct. 28; 269(43):27051-8). However, the constant CoA level maintained within cells may be a barrier to the effective production of O-acetyl homoserine through acetyl-CoA. It is reported that the substitution of arginine R at position 106 with alanine A alters pantothenate kinase from being sensitive to feedback inhibition by CoA to being refractory thereto (JOURNAL OF BACTERIOLOGY, 185, June 2003, p. 3410-3415). The wild-type protein was found to retain only about 20% of the catalytic activity in the presence of 40 mM CoA whereas no decreases were detected in the catalytic activity of the R106A mutant protein at the same concentration of CoA. Further, a mutant strain which expressed the mutant protein was found to have significantly higher intracellular levels of CoA, compared to the wild-type.

Leading to the present invention, intensive and thorough research, conducted by the present inventors, resulted in the finding that the introduction and enhancement of either or both of (a) the pantothenate kinase gene refractory to feedback inhibition by CoA and (b) the O-acetyl CoA synthase gene results in a significant improvement in the productivity of O-acetyl homoserine.

SUMMARY OF THE INVENTION

It is therefore an object of the present invention to provide a microorganism strain capable of producing O-acetyl homoserine in high yield, which is designed to fortify an acetyl-CoA biosynthesis pathway by overexpressing an acs gene and a coaA gene refractory to feedback inhibition by CoA.

It is another object of the present invention to provide a method of producing O-acetyl homoserine in high yield, using the microorganism strain.

In accordance with an aspect of the present invention, there is provided a strain of *Escherichia* sp. capable of producing O-acetyl homoserine, with the introduction and enhancement therein of:

(a) an acetyl-CoA synthase gene (acs);

(b) a pantothenate kinase gene (coaA) encoding a pantothenate kinase gene refractory to feedback inhibition by CoA; or (c) both the acetyl-CoA synthase gene (acs) of (a) and the pantothenate kinase gene (coaA) of (b).

In accordance with another aspect of the present invention, there is provided a method of producing O-acetyl homoserine in a culture medium, comprising fermenting the strain in the culture medium.

In accordance with a further aspect of the present invention, there is a method of producing L-methionine and acetate, comprising: (a) fermentating the strain of *Escherichia* sp. to produce O-acetyl homoserine; (b) separating the O-acetyl homoserine; and (c) converting the O-acetyl homoserine, together with methyl mercaptan, into L-methinoine and acetate in the presence of an enzyme selected from a group consisting of cystathionine gamma synthase, O-acetyl homoserine sulfhydrylase, and O-succinyl homoserine sulfhydrylase.

According to the present invention, therefore, O-acetyl homoserine can be produced in high yield biologically, which is more environmentally friendly than are chemical methods. In addition, the O-acetyl-L-homoserine produced by the strain of the present invention can be converted into L-methionine and acetate enzymatically, e.g., by O-acetyl-homoserine sulfhydrylase. L-methionine is useful as an additive for food or animal feed.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1:
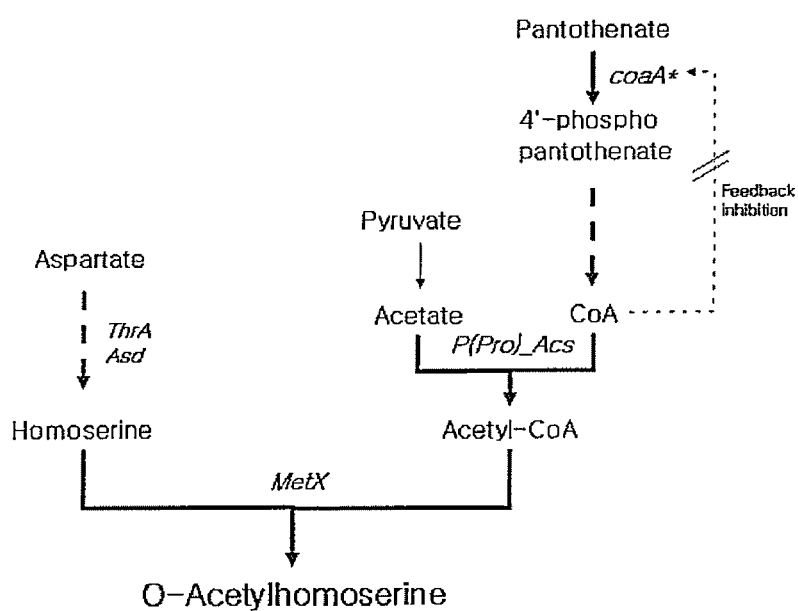
FIG. 1 is a schematic view showing an O-acetyl-homoserine biosynthesis pathway through which O-acetyl-homoserine can be produced in high yield.

In accordance with an aspect thereof, the present invention provides a strain of *Escherichia* sp. capable of producing O-acetyl homoserine, with the introduction and enhancement therein of (a) an acetyl-CoA synthase gene (acs); (b) a pantothenate kinase gene (coaA) encoding a pantothenate kinase gene refractory to feedback inhibition by CoA; or (c) both the acetyl-CoA synthase gene (acs) of (a) and the pantothenate kinase gene (coaA) of (b).

As used herein, the term "L-methionine precursor" is intended to refer to a metabolite found on the methionine biosynthesis pathway or a derivative thereof, and particularly to O-acetyl homoserine.

As used herein, the term "O-acetyl homoserine-producing strain" is intended to refer to a eukaryotic or prokaryotic microorganism which can produce O-acetyl homoserine intracellularly or extracelluarly and particularly to a genetically modified microorganism which can accumulate O-acetyl homoserine therein. Examples of the strain useful in the present invention include *Escherichia* sp., *Erwinia* sp., *Serratia* sp., *Providencia* sp., *Corynebacteria* sp., *Pseudomonas* sp., *Leptospira* sp., *Salmonellar* sp., *Brevibacteria* sp., *Hypomononas* sp., *Chromobacterium* sp., *Norcardia* sp., fungi and yeasts, with preference for *Escherichia* sp., *Corynebacteria* sp. and *Leptospira* sp. and yeast. More preferred is *Escherichia* sp. Far more preferred is *Escherichia coli*. Further far more preferred is a strain of *E. coli* which can produce lysine, threonine, isoleucine or methionine. Most preferred is the *E. coli* strain (Accession No. KCCM 10921P) which is derived from the threonine-producing strain described in U.S. Ser. No. 12/062,835 with the introduction of thrA and metX genes thereinto to improve the O-acetyl-L-homoserine biosynthesis pathway.

In a preferred embodiment of the present invention, provided is an O-acetyl homoserine-producing strain which is improved in the productivity of O-acetyl homoserine through the fortification of acetyl-CoA biosynthesis pathway with the introduction of an acetyl-CoA synthase gene involved in acetyl-CoA biosynthesis pathway into the strain and the enhancement thereof.

In another preferred embodiment of the present invention, provided is an O-acetyl homoserine-producing strain which is improved in the productivity of O-acetyl homoserine through the fortification of acetyl-CoA biosynthesis pathway with the introduction of a panthotenate kinase gene refractory to feedback inhibition by CoA accumulation into the strain and the enhancement thereof.

In a further preferred embodiment of the present invention, provided is an O-acetyl homoserine-producing strain which has improved the productivity of O-acetyl homoserine through the fortification of acetyl-CoA biosynthesis pathway with the introduction of both an acetyl-CoA synthase gene involved in acetyl-CoA biosynthesis pathway and a panthotenate kinase gene refractory to feedback inhibition by CoA accumulation into the strain and enhancement thereof.

As used herein, the term "introduction and enhancement" is intended to mean an increase in the intracellular activity of an enzyme encoded by the corresponding gene, which can be generally achieved by the overexpression of the gene. There are many approaches to the overexpression of a target gene. For example, the overexpression may be implemented by the modification of a base in the promoter region and/or 5'-UTR for the target gene, by the introducing the extra copy of the target gene on the chromosomae, or by the introduction of the target gene in combination with an autologous or a heterologous promoter onto a vector, followed by the transformation of the vector into a microorganism strain. Further, a mutation in the ORF (open reading frame) of the target gene may result in the overexpression thereof. In numerical terms, when overexpression occurs, the corresponding protein increases in activity or concentration by 10%, 25%, 50%, 75%, 100%, 150%, 200%, 300%, 400%, or 500%, 1000% or up to 2000%, compared to when it is expressed in a natural state.

For the introduction and enhancement of a gene, a strong promoter, a mutation in the corresponding promoter or an increase in the number of gene copies may be taken. Preferable is the use of a strong promoter. So long as it is a constitutive one, any promoter may be used in the present invention without limitations imparted thereto. Useful are pTac, pTrc, pPro, pR, and pL, with pPro of SEQ ID NO. 9 being most preferred. The target gene may comprise the pPro promoter of SEQ ID NO. 9, wholly or partially.

The enzymes acetyl-CoA synthase and pantothenate kinase may come from a variety of different microorganisms and are encoded by genes termed "acs" and "coaA" in the present invention, respectively.

In the present invention, a microorganism strain with high capability of producing O-acetyl homoserine in which a modification is made to fortify acetyl-CoA synthase activity and a method for producing O-acetyl homoserine using the same are provided.

In an embodiment of the present invention, the O-acetyl homoserine-producing strain is prepared as follows.

In order to increase the productivity of O-acetyl-L-homoserine, a promoter for the gene encoding acetyl-CoA synthase in a strain is substituted with the constitutive promoter P (pro) of SEQ ID NO. 9, followed by the construction of a constitutive expression plasmid to induce the overexpression of the target gene without catabolite repression. The gene coding for acetyl-CoA synthase is generally expressed as acs. It may be obtained from the genome sequence (gi:89110790) of *Escherichia coli* disclosed previously (Mol Syst Biol. 2006; 2:2006.0007. Epub 2006 Feb. 21.). Also, the gene sequence may be obtained from public databases such as those constructed by the National Center for Biotechnology Information (NCBI) or the DNA Data Bank of Japan (DDBJ).

Acetyl-CoA synthase has the activity of catalyzing the following reaction. If enhanced, the expression of the gene coding for the enzyme induces the intracellular accumulation of acetyl-CoA.

Acetate+CoA<=>Acetyl–CoA

Next, the strain harboring the constitutive expression plasmid is manipulated to further increase the synthesis of acetyl-CoA. The approach taken in this invention is to incapacitate the feedback inhibition against CoA synthesis. In this context, pantothenase kinase, which catalyzes the first committed step and is the rate-controlling enzyme in CoA biosynthesis, is mutated to be refractory to feedback inhibition by CoA. For this, a mutation is introduced into the gene coding for pantothenate kinase, that is, coaA (R106A). This gene may be obtained from the genome sequence (gi:89110060) of *Escherichia coli* disclosed previously (Mol Syst Biol. 2006; 2:2006.0007. Epub 2006 Feb. 21.). Also, the gene sequence may be obtained from public data bases such as those constructed by the National Center for Biotechnology Information (NCBI) or the DNA Data Bank of Japan (DDBJ).

In addition to having the activity of catalyzing the phosphorylation of pantothenase to 4-phosphopantothenate as shown in the following reaction, the mutated pantothenate kinase is insensitive to feedback inhibition by CoA. Hence, the enhancement of the gene coding for the mutated pantothenase kinase increases the intracellular level of the CoA pool.

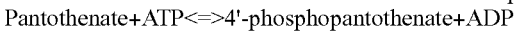

Pantothenate+ATP<=>4'-phosphopantothenate+ADP

The mutant strain thus obtained accumulates lots of CoA and acetyl-CoA therein which are used as substrates, along with homoserine, for the production of O-acetyl-L-homoserine by the enzyme encoded by metX. Therefore, the mutant strain can produce O-acetyl-L-homoserine in high yield.

As such, three O-acetyl homoserine-producing strains, CJM-X/pthrA(M)-CL(pCL-Pro-Acs), CJM-X/pthrA(M)-CL(pCL-Pro-coaA(R106A)) and CJM-X/pthrA(M)-CL(pCL-Pro-acs, pACYC-coaA(R106A)), were named "*Escherichia coli* CA05-0565", "*Escherichia coli* CA05-0564" and "*Escherichia coli* CA05-0566", respectively, and were prepared and deposited at KCCM (Korean Culture of Microorganism, Eulim build, Hongje-1-Dong, Seodaemunku, Seoul, 361-221, Korea) on Aug. 11, 2009, with the accession Nos. KCCM11023P, KCCM11022P, and KCCM11024P, respectively.

In a preferred embodiment of the present invention, provided is an O-acetyl homoserine-producing strain in which acs, a gene involved in the biosynthesis of acetyl-CoA, is overexpressed under the control of the constitutive promoter Pro. In more detail, the pRro promoter is composed of the full-length sequence of or a part of SEQ ID NO. 9.

In another preferred embodiment of the present invention, provided is an O-acetyl homoserine-producing strain in which a pantothenate kinase responsible for the committed step of CoA biosynthesis is refractory to feedback inhibition by CoA. Also, a method for producing O-acetyl homoserine in high yield is provided. Preferably, the pantothenate kinase refractory to feedback inhibition by CoA is mutated at amino acid position 106. More preferably, the pantothenate kinase is mutated at amino acid position 106 by the substitution of arginine with alanine, thus being refractory to feedback inhibition by CoA. Most preferably, the pantothenate kinase refractory to feedback inhibition by CoA has the amino acid sequence of SEQ ID NO. 8.

In a further preferred embodiment of the present invention, provided is an O-acetyl homoserine producing E. coli strain in which the two approaches are taken together to enhance both the acetyl-CoA synthase activity and the pantothenate kinase activity.

Preferably, the E. coli strain useful for the preparation of the O-acetyl homoserine-producing strain is one capable of producing lysine, threonine, isoleucine, or methionine. More preferably, the E. coli strain features the introduction and enhancement of (a) homoserine acetyl transferase; (b) aspartokinase or homoserine dehydrogenase activity; or (c) both (a) and (b). Most preferable is E. coli CJM-X/pthrA(M)—CL (Accession No. KCCM 10921P).

Figure 2:
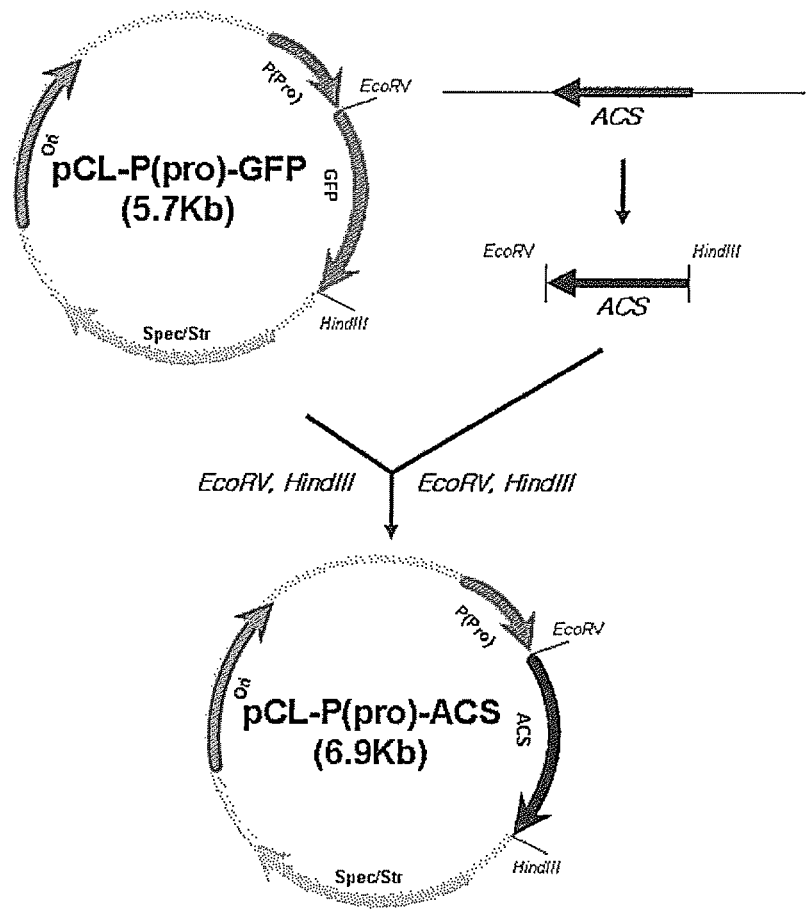
FIG. 2 is a schematic view showing the genetic map and construction of an expression vector pCL-P(pro)-acs carrying an acetyl-CoA synthase gene(acs)

In a concrete example of the present invention, the acs gene is cloned and used to construct the acs expression vector pCL-P(pro)-acs which is under the control of the constitutive promoter pPro of SEQ ID NO. 9 (FIG. 2). A coaA gene is mutated at amino acid position 106 from arginine to alanine to give a mutant coaA gene of SEQ ID NO. 8 which encodes the enzyme refractory to feedback inhibition by CoA. This mutant gene is cloned into plasmids carrying the constitutive promoter pPro of SEQ ID NO. 9, so as to afford recombinant expression plasmids, pCL-P(pro)-coaA(R106A) and pACYC-coaA(R106A) (FIG. 3) which are under the control of the constitutive promoter pPro. The recombinant plasmids pCL-P(pro)-acs, and either pCL-P(pro)-coaA(R106A) or pACYC-coaA(R106A) are transformed, alone or in combination, into CJM-X which was constructed by removing pthrA(M)-CL plasmid from CJM-X/pthrA(M)-CL (Accession No. KCCM 10921P), a strain with an enrichment in thrA and metX as disclosed in U.S. Ser. No. 12/062,835, to prepare O-acetyl homoserine-producing strains which features the introduction and enrichment of (a) a gene coding for acetyl-CoA synthase (acs), (b) a gene coding for pantothenate kinase refractory to feedback inhibition by CoA (coaA) and (c) both (a) and (b) genes (Examples 1 to 3). Flask cultivation showed that, compared to the control CJM-X, O-acetyl homoserine productivity was increased by 2.8 g/L for production quantity and by 4.7% for production yield in the strain transformed with the pCL-P(pro)-acs carrying the acetyl-CoA synthase gene (acs) of (a), by 2.1 g/L for production quantity and by 3.5% for production yield in the strain transformed with pCL-P(pro)-coaA(R106A) carrying the pantothenate kinase refractory to feedback inhibition by CoA of (b) (coaA), and by 6.8 g/L for production quantity and by 11.4% for production yield in the strain transformed with both pCL-P(pro)-acs and pACYC-coaA(R106A) of (b) and (c) (Example 2, Table 2).

In accordance with another aspect thereof, the present invention is directed to a method for producing O-acetyl-homoserine, comprising the fermentation of the O-acetyl-homoserine producing E. coli strain in a culture medium to accumulate O-acetyl-homoserine in the medium.

In accordance with a further aspect thereof, the present invention is directed to a method of producing L-methionine and acetate, comprising (a) producing O-acetyl-homoserine through the fermentation of the O-acetyl homoserine-producing a strain of Escherichia sp. of the present invention; (b) separating the O-acetyl homoserine; and (c) converting the separated O-acetylhomoserine, together with methylmercaptan, into L-methionine and acetate in the presence of a transferase selected from among cystathionine gamma synthase, O-acetylhomoserine sulfhydrylase and O-succinylhomoserine sulfhydrylase.

When in connection with the strain of the present invention, the method of producing L-methionine, which is based on the use of the converting enzyme, cystathionine gamma synthase, O-acetylhomoserine sulfhydrylase or O-succinyl-homoserine sulfhydrylase as disclosed in WO 2008/013432, issued to the present inventors, can bring about a higher yield in L-methionine production.

The O-acetyl-L-homoserine-producing strain prepared above can be cultured in a medium and conditions known in the art. As is well understood by those familiar with the art, the culture method may be adjusted according to the strain used. The fermentation may be carried out in a batch, a continuous culture, or a fed-batch type, but is not limited thereto. A variety of fermentation methods are described in the following reference: "Biochemical Engineering" by James M. Lee, Prentice-Hall International Editions, pp 138-176.

The culture medium has to meet the culture conditions for a specific strain. A variety of microorganism culture mediums are described in the following reference: "Manual of Methods for General Bacteriology" by the American Society for Bacteriology, Washington D.C., USA, 1981. Generally, a culture medium includes various carbon sources, nitrogen sources and trace elements. Examples of the carbon source include carbohydrates such as glucose, sucrose, lactose, fructose, maltose, starch and cellulose; fats such as soybean oil, sunflower oil, castor oil and coconut oil; fatty acids such as palmitic acid, stearic acid, and linoleic acid; alcohols such as glycerol and ethanol; and organic acids such as acetic acid. These carbon sources may be used alone or in combination. Examples of the nitrogen source include organic nitrogen sources, such as peptone, yeast extract, gravy, malt extract, corn steep liquor (CSL) and bean flour, and inorganic nitrogen sources such as urea, ammonium sulfate, ammonium chloride, ammonium phosphate, ammonium carbonate and ammonium nitrate, which may be used alone or in combination. Additionally, the medium may contain potassium dihydrogen phosphate, dipotassium hydrogen phosphate and/or the corresponding sodium-containing salts thereof. Also, metal may be contained in the form of salts, like magnesium sulfate or iron sulfate, in the medium. In adition, amino acids, vitamins and proper precursors can be added as well. The mediums or the precursors can be added to the culture by batch-type or continuous type.

The pH of the culture can be adjusted with a suitable compound, for example, ammonium hydroxide, potassium hydroxide, ammonia, phosphate acid, and sulfuric acid. In order to inhibit the generation of bubbles in the culture, a defoaming agent such as fatty acid polyglycol ester may be used. To create aerobic conditions, the culture medium may be aerated with oxygen or oxygen-containing gas (e.g., air). The culture medium is maintained at 20~45° C. and preferably at 25~40° C. The strain is cultured to a desired level of the L-methionine precursor preferably for 10~160 hrs.

A better understanding of the present invention may be obtained through the following examples which are set forth to illustrate, but are not to be construed as limiting the present invention.

Example 1

Preparation of O-Acetyl Homoserine Producing Strain

<1-1> Cloning of acs Gene

For acs gene cloning, the acs gene encoding acetyl-CoA synthase was amplified by PCR with the genomic DNA of Escherichia coli W3110 (ATCC 27325) serving as a template. The base sequence of the acs gene was obtained from the GenBank database of the NIH (NCBI-gi:89110790) and is expressed in SEQ ID NO. 7. On the basis of the base sequence, an ORF ranging from ATG to TAA was PCR amplified using a set of primers (SEQ ID NOS. 1 and 2) containing the restriction enzyme sites EcoRV and HindIII while the genomic DNA of Escherichia coli W3110 was used as a template in the presence of the high-fidelity DNA polymerase PfuUltra™ (Stratagene). The PCR was performed with 30 cycles of denaturation at 96° C. for 30 sec, annealing at 50° C. for 30 sec, and extension at 72° C. for 2 min to synthesize an about 2.0 kb acs gene containing EcoRV and HindIII sites therein.

After digestion with the restriction enzymes EcoRV and HindIII, the amplified acs gene was ligated to a pPro-GFP vector which was previously treated with the same restriction enzymes, so as to construct a recombinant constitutive expression vector carrying the acs gene and containing the constitutive promoter Pro, termed pCL-P(pro)-acs. FIG. 2 shows the genetic map and construction of the expression vector pCL-P(pro)-acs.

<1-2> Cloning of Feedback Resistant coaA Gene

For the cloning of a feedback-resistant acs gene, a coaA gene encoding pantothenate kinase acetyl-CoA synthase refractory to feedback inhibition by CoA was amplified by PCR with the genomic DNA of Escherichia coli W3110 (ATCC 27325) serving as a template. For this, first, the base sequence of a coaA gene was obtained from the GenBank database of the NIH (NCBI-gi:89110060). On the basis of the base sequence, a set of primers (SEQ ID NOS. 3 and 4) for the PCR amplification of a coaA fragment from ATG to TAA was designed to contain the restriction enzyme site EcoRV and the codon GCC, instead of CGT of nucleotide positions 316-318, to impart resistance to feedback inhibition by CoA. Separately, a set of primers (SEQ ID NOS. 5 and 6) for the PCR amplification of a coaA fragment was designed to contain the restriction enzyme site HindIII and the codon GCC, instead of CGT of nucleotide positions 316~318 for the same reason as described above.

While the genomic DNA of Escherichia coli W3110 was used as a template, PCR was performed using the respective synthesized primer sets (SEQ ID NOS. 3 and 4, and SEQ ID NOS. 5 and 6) in the presence of the high-fidelity DNA polymerase PfuUltra™ (Stratagene), with 30 cycles of denaturation at 96° C. for 30 sec, annealing at 50° C. for 30 sec, and extension at 72° C. for 2 min. As a result, two gene fragments were obtained: one was about 344 bp in size extending from the initial ATG codon of coaA, with a mutation from the CGT codon to the GCC codon at nucleotide positions 316 to 318; the other was about 642 bp in size, containing the stop codon TAA, with a mutation from the CGT codon to the GCC codon at nucleotide positions 316 to 318.

While the two fragments were used as templates, PCR was carried out with 10 cycles of denaturation at 96° C. for 60 sec, annealing at 50° C. for 60 sec, and extension at 72° C. for 2 min, followed by 20 cycles of the same thermal conditions using a set of the primers of SEQ ID NOS. 3 and 6. As a result, a 963-bp gene in which the codon GCC was substituted for the codon CGT at positions 316 to 318 was obtained (coaA (R106A)).

After digestion with the restriction enzymes EcoRV and HindIII, the mutant coaA gene was cloned by ligation to a pPro-GFP vector to construct a recombinant expression vector, termed pCL-P(pro)-coaA(R106A), which was under the control of the constitutive promoter Pro and carried a mutant coaA gene in which the codon for an amino acid residue at position 106 was mutated from CGT to GCC. The mutant coaA amino acid sequence is expressed in SEQ ID NO. 8.

Figure 3:
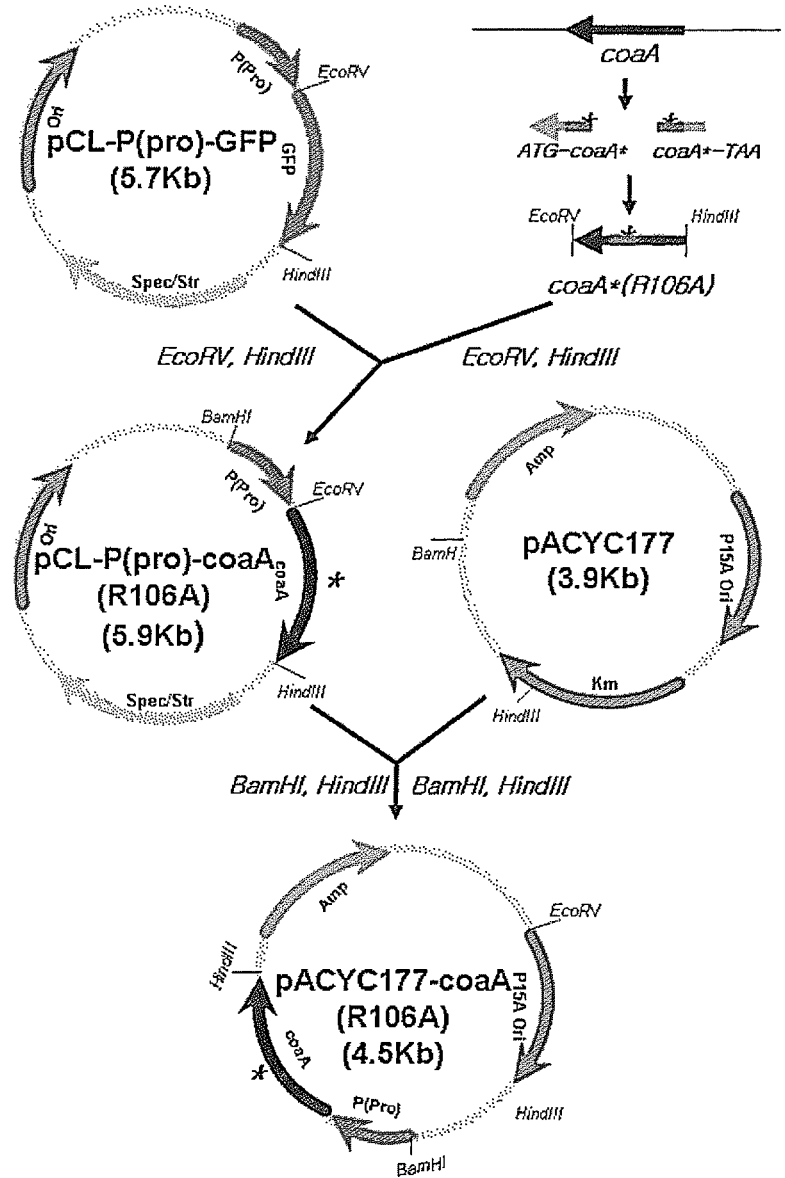
FIG. 3 is a schematic view showing the genetic map and construction of the expression vectors pCL-P(pro)-coaA (R106A) and pACYC-coaA(R106A), both carrying a gene encoding pantothenate kinase refractory to feedback inhibition by CoA (coaA(R106A)).

Next, the mutant coaA gene was cloned into a pACYC177 vector. The recombinant plasmid pCL-P(pro)-coaA(R106A) was treated with the restriction enzymes to excise a 1.45 kb coaA(R106A) fragment containing the Pro promoter therefrom. The coaA(R106A) fragment was inserted into a pACYC177 vector which was previously treated with BamHI and HindIII to afford a recombinant vector pACYC-coaA (R106A). In FIG. 3, the construction of the recombinant expression vectors pCL-P(pro)-coaA(R106A) and pACYC-coaA(R106A) is schematically illustrated.

<1-3> Preparation of O-Acetyl-Homoserine-Producing Strain

The plasmids constructed in Examples <1-1> and <1-2>, pCL-P(pro)-acs, and pCL-P(pro)-coaA(R106A), were transformed into the strain CJM-X, which was constructed by removing pthrA(M)-CL plasmid from CJM-X/pthrA(M)-CL (Accession No. KCCM 10921P) disclosed in U.S. Ser. No. 12/062,835, followed by incubation on LB-Sp (Yeast extract 10 g/L, NaCl 5 g/L, Tryptone 10 g/L, Spectinomycin 25 µg/L) to select 10 spectinomycin-resistant colonies for each transformant. Additionally, the CJM-X anchoring the pCL-P(pro)-acs vector was transformed with the recombinant expression plasmid constructed in Example <1-2>, pACYC-coaA (R106A), and cultured on LB-Sp-Ap (Yeast extract 10 g/L, NaCl 5 g/L, Tryptone 10 g/L, Spectinomycine 25 µg/L, Ampicillin 50 µg/L) to select 10 colonies resistant to both spectinomycin and ampicillin. They were compared to each other for O-acetyl homoserine productivity.

Example 2

Fermentation for O-Acetyl Homoserine Production

In order to examine the strains prepared in Example 1 for ability to produce the methionine precursor O-acetyl homoserine, they were cultured in Erlenmeyer flasks.

For this culture, the O-acetyl-homoserine titer medium shown in Table 1 was employed.

TABLE 1

Composition of Medium for O-Acetyl-Homoserine Production

| Composition | Concentration(per liter) |
| --- | --- |
| Glucose | 60 g |
| Ammonium Sulfate | 17 g |
| $KH_2PO_4$ | 1.0 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| $CaCO_3$ | 30 g |
| Yeast Extract | 2 g |
| Methionine | 0.15 g |
| Threonine | 0.15 g |

Single colonies which were generated on LB plates during incubation overnight at 32° C. were taken with platinum loops and inoculated respectively into 25 mL of the O-acetyl homoserine titer medium, followed by culturing at 32° C. for 42~64 hrs with shaking at 250 rpm. Each culture was quantitatively analyzed for O-acetyl homoserine using HPLC. The analysis data are summarized in Table 2, below.

Compared to the control strain CJM-X, as shown in Table 2, the quantity and production yield of O-acetyl homoserine was found to increase by 2.8 g/L and 4.7%, respectively, upon the overexpression of the acs gene under the control of the constitutive expression promoter P(pro), by 2.1 g/L and 3.5%, respectively, upon the overexpression of the feedback inhibition-refractory coaA(R106A) gene, and by 6.8 g/L and 11.4%, respectively, upon the concomitant overexpression of both the acs and coaA(R106A).

Taken together, the data obtained in the flask tests indicate that the introduction and enhancement of either or both the acs gene and the feedback inhibition-refractory coaA gene leads to an increase in the productivity and production yield of O-acetyl homoserine.

TABLE 2

Effects of Expression of Acs and CoaA(R106) on O-Acetyl-Homoserine Production

| Strain | Plasmid | OAH production (g/L) | Yield (%) |
| --- | --- | --- | --- |
| CJM-X | — | 17.5 | 29.1 |
| | pCL-P(pro)-acs | 20.3 | 33.8 |
| | pCL-P(pro)-coaA(R106A) | 19.6 | 32.6 |
| | pCL-P(pro)-acs pACYC-coaA(R106A) | 24.3 | 40.5 |

INDUSTRIAL APPLICABILITY

As described hitherto, the present invention provides a strain of *Escherichia* sp. which produces O-acetyl homoserine in high yield in a culture medium when fermented in the medium. In addition, the O-acetyl homoserine can be converted, along with methyl mercaptan, into L-methionine in the presence of a methionine-converting enzyme, with the concomitant production of acetic acid.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A strain of *Escherichia* sp. capable of producing O-acetyl homoserine, wherein the strain of *Escherichia* sp. overexpresses (a) a gene encoding a polypeptide having acetyl-CoA synthase activity and (b) a gene encoding a polypeptide having homoserine O-acetyl transferase activity.

2. The strain of *Escherichia* sp. according to claim 1, wherein gene (a) and/or (b) is introduced and enhanced by employing a new promoter or a mutant promoter or by increasing a number of the gene.

3. The strain of *Escherichia* sp. according to claim 2, wherein the new promoter is selected from a group consisting of pTrc, pPro, pR and pL.

4. The strain of *Escherichia* sp. according to claim 3, wherein the promoter is a pPro promoter having a base sequence of SEQ ID NO. 9, or a part thereof.

5. The strain of *Escherichia* sp. according to claim 1, wherein the strain further overexpresses a gene encoding a mutated pantothenate kinase that (a) is refractory to feedback inhibition by CoA, and (b) has an amino acid sequence of SEQ ID NO. 8.

6. The strain of *Escherichia* sp. according to claim 1, wherein the strain is derived from *Escerichia coil* CJM-X deposited with Accession No. KCCM 10921P by modifying *Escerichia colt* CJM-X to overexpress the gene encoding a polypeptide having acetyl-CoA synthase activity.

7. The strain of *Escherichia* sp. according to claim 1, wherein the strain is *Escherichia coli* CA05-0565 deposited with (Accession No. KCCM11023P).

8. The strain of *Escherichia* sp. according to claim 1, wherein the strain is *Escherichia coli* CA05-0566 deposited with (Accession No. KCCM11024P).

9. The strain of *Escherichia* sp. according to claim 1, belonging to *Escherichia coli*.

10. A method of producing O-acetyl homoserine, comprising:
fermenting the strain of *Escherichia* sp. according to claim 1 in a culture medium to produce O-acetyl homoserine; and
separating the O-acetyl homoserine from the culture medium.

* * * * *

UNITED STATES PATENT AND TRADEMARK OFFICE
CERTIFICATE OF CORRECTION

PATENT NO. : 8,609,396 B2
APPLICATION NO. : 12/550099
DATED : December 17, 2013
INVENTOR(S) : So Young Kim et al.

Page 1 of 1

It is certified that error appears in the above-identified patent and that said Letters Patent is hereby corrected as shown below:

In the Claims

Column 18, Line 39:
Claim 7, "with (Accession No. KCCM11023P)." should read, --with Accession No. KCCM11023P.--.

Column 18, Line 42:
Claim 8, "with (Accession No. KCCM11024P)." should read, --with Accession No. KCCM11024P.--.

Signed and Sealed this
Twenty-third Day of September, 2014

Michelle K. Lee
*Deputy Director of the United States Patent and Trademark Office*